US009759703B2

(12) United States Patent
Ediger et al.

(10) Patent No.: US 9,759,703 B2
(45) Date of Patent: Sep. 12, 2017

(54) SYSTEMS AND METHODS FOR MEASURING GAS FLUX

(71) Applicant: LI-COR, Inc., Lincoln, NE (US)

(72) Inventors: Kevin Ediger, Lincoln, NE (US); Bradley Alan Riensche, Firth, NE (US)

(73) Assignee: Li-Cor, Inc., Lincoln, NE (US)

( * ) Notice: Subject to any disclaimer, the term of this patent is extended or adjusted under 35 U.S.C. 154(b) by 596 days.

(21) Appl. No.: 14/039,686

(22) Filed: Sep. 27, 2013

(65) Prior Publication Data

US 2015/0090000 A1 Apr. 2, 2015

(51) Int. Cl.
*G01N 33/00* (2006.01)
*H04L 12/403* (2006.01)
*H04J 3/06* (2006.01)

(52) U.S. Cl.
CPC ........ *G01N 33/0075* (2013.01); *H04J 3/0658* (2013.01); *H04L 12/403* (2013.01); *H04J 3/0644* (2013.01); *H04J 3/0667* (2013.01)

(58) Field of Classification Search
CPC .. G01N 33/0075; H04J 3/0644; H04J 3/0658; H04J 3/0667; H04L 12/403
See application file for complete search history.

(56) References Cited

U.S. PATENT DOCUMENTS

| | | | |
|---|---|---|---|
| 4,288,062 A | 9/1981 | Gupta et al. | |
| 5,566,180 A | 10/1996 | Eidson et al. | |
| 5,670,999 A | 9/1997 | Takeuchi et al. | |
| 5,838,008 A | 11/1998 | Esler et al. | |
| 5,907,685 A * | 5/1999 | Douceur | G04G 7/00 709/248 |
| 6,121,617 A | 9/2000 | Hirayama et al. | |
| 6,243,657 B1 * | 6/2001 | Tuck | G01N 29/2412 324/207.13 |

(Continued)

FOREIGN PATENT DOCUMENTS

| | | |
|---|---|---|
| CA | 2461472 A1 | 4/2003 |
| CN | 1561590 | 1/2005 |

(Continued)

OTHER PUBLICATIONS

Li, Y., et al. "Time Synchronisation Analysis of an FPGA based GPS/INS Integrated System." International Global Navigation Satellite Systems Society IGNSS Symposium, Surfers Paradise, Australia. 2006.*

(Continued)

*Primary Examiner* — Lisa Caputo
*Assistant Examiner* — Punam Roy
(74) *Attorney, Agent, or Firm* — Leydig, Voit & Mayer, Ltd.; Gerald T. Gray (57) ABSTRACT

Systems and methods for measuring gas flux are disclosed. One method for calculating gas flux includes: receiving a master clock signal from a global positioning system (GPS) module; transmitting a clock synchronization signal that is based on the master clock signal to a measurement subsystem configured to measure environmental data, wherein the measurement subsystem comprises at least two clocks; receiving the environmental data from the measurement subsystem, wherein the environmental data is associated with the at least two clocks; and calculating gas flux based on the environmental data received from the measurement subsystem.

22 Claims, 5 Drawing Sheets

(56) References Cited

U.S. PATENT DOCUMENTS

| | | | |
|---|---|---|---|
| 6,252,445 B1 | 6/2001 | Eidson | |
| 6,278,710 B1 | 8/2001 | Eidson | |
| 6,317,212 B1 | 11/2001 | Eckles | |
| 6,369,387 B1 | 4/2002 | Eckles | |
| 6,370,159 B1 | 4/2002 | Eidson | |
| 6,772,361 B1* | 8/2004 | Walsh | G06F 1/14 713/502 |
| 7,365,352 B2 | 4/2008 | Muta et al. | |
| 8,199,635 B2* | 6/2012 | Taylor | H04L 67/12 370/217 |
| 8,433,525 B2 | 4/2013 | Burba et al. | |
| 9,160,472 B2* | 10/2015 | Chandhoke | H04J 3/06 |
| 2001/0045521 A1 | 11/2001 | Prozzo et al. | |
| 2001/0048079 A1 | 12/2001 | Brunamoti et al. | |
| 2004/0187043 A1* | 9/2004 | Swenson | G06F 1/12 713/400 |
| 2004/0249982 A1 | 12/2004 | Arnold et al. | |
| 2004/0258097 A1 | 12/2004 | Arnold et al. | |
| 2005/0066211 A1* | 3/2005 | Heinrich | H04J 3/0638 713/375 |
| 2006/0151680 A1* | 7/2006 | Franzen | A01D 34/006 250/205 |
| 2006/0192097 A1 | 8/2006 | Anttalainen | |
| 2010/0110437 A1 | 5/2010 | Furtaw et al. | |
| 2010/0110438 A1 | 5/2010 | Furtaw | |
| 2012/0153166 A1 | 6/2012 | Gueorguiev et al. | |
| 2012/0290266 A1* | 11/2012 | Jain | G06F 19/3406 702/187 |
| 2013/0201316 A1* | 8/2013 | Binder | H04L 67/12 348/77 |
| 2015/0078405 A1* | 3/2015 | Roberts | H04J 3/0658 370/509 |
| 2017/0099634 A1* | 4/2017 | Garudadri | H04W 52/0209 |

FOREIGN PATENT DOCUMENTS

| | | | | |
|---|---|---|---|---|
| CN | 103001720 A | * | 3/2013 | H04J 3/0641 |
| DE | 10147422 A1 | | 4/2003 | |
| DE | 10229110 A1 | | 4/2006 | |
| EP | 1430627 A1 | | 4/2003 | |
| EP | 1430628 A1 | | 6/2004 | |
| EP | 2445127 A1 | * | 4/2012 | H04J 3/0667 |
| JP | 2008-116263 A | | 7/1996 | |
| JP | 8-273939 A | | 10/1996 | |
| JP | 11-307705 A | | 11/1999 | |
| KR | 10-2006-0050193 A | | 5/2006 | |
| WO | WO 03/028258 A1 | | 4/2003 | |
| WO | WO 03/028259 A1 | | 4/2003 | |

OTHER PUBLICATIONS

Aram, S.; Troiano, A.; Pasero, E., "Environment sensing using smartphone," in Sensors Applications Symposium (SAS), 2012 IEEE, pp. 1-4, Feb. 7-9, 2012.*

Baldocchi, Dennis, et al. "FLUXNET: A new tool to study the temporal and spatial variability of ecosystem-scale carbon dioxide, water vapor, and energy flux densities." Bulletin of the American Meteorological Society 82.11 (2001): 2415-2434.*

Tao, Barry, Jon Campbell, and Gwyn Griffiths. "Distributed sensor relay system for near real time observation, control and data management on a scientific research ship." Networked Digital Technologies. Springer Berlin Heidelberg, 2012. 519-535.*

Yelland, M. J., et al. "AutoFlux: an autonomous system for the direct measurement of the air-sea fluxes of CO2, heat and momentum." Journal of Operational Oceanography 2.1 (2009): 15-23.*

Hall, P. G., E. J. Dumas, and D. L. Senn. "NOAA ARL Mobile Flux Platform Instrumentation Integration on University of Alabama Sky Arrow Environmental Aircraft." National Oceanic and Atmospherric Administration Technical Memorandum ARL-257. (2006): 1-56.*

Fairall, C. W., et al. "Measurement and parameterization of air-sea gas transfer." Boundary Layer Meteorol 96 (2000): 63-105.*

Behn, Mario, Vincent Hohreiter, and Andreas Muschinski. "A scalable datalogging system with serial interfaces and integrated GPS time stamping."Journal of Atmospheric and Oceanic Technology 25.9 (2008): 1568-1578.*

Hazen, David G. "UDATS-II: data acquisition in a client-server environment."Oceanic Engineering, IEEE Journal of 21.3 (1996): 305-312.*

Hansen, Frank. "Utilizing FPGAs in an IEEE 1588 Precision Time Control Implementation," EE Times. Mar. 30, 2007. Accessed online at <http://www.eetimes.com/document.asp?doc_id=1274040>.*

"LI-7500A Open Path CO2/H2O Anaylyzer: Advantages," Li-COR® <www.licor.com/env/products/gas_analysis/LI-7500A/>, Sep. 8, 2012, Accessed online at <www.archive.org>.*

Burba, G. G., D. J. Anderson, and J. L. Amen. "Eddy Covariance Method: Overview of General Guidelines and Conventional Workflow." AGU Fall Meeting Abstracts. 2007.*

Gu, Lianhong, et al. "The fundamental equation of eddy covariance and its application in flux measurements." Agricultural and Forest Meteorology 152 (2012): 135-148.*

NIST and IEEE Instrumentation and Measurement Society, "Workshop on IEEE-1588, Standard for a Precision Clock Synchronization Protocol for Networked Measurement and Control Systems," Gaithersburg, Maryland (Sep. 24, 2003).

Burba, G., et al., Correcting Apparent Off-Season CO2 Uptake Due to Surface Heating of an Open Path Gas Analyzer: Progress Report of an Ongoing Study, American Meteorological Society, 27th Conference on Agricultural and Forest Meteorology (2006).

Burba et al., "Introduction to the Eddy Covariance Method" [Presentation], Copyright 2007-2009 LI-COR, Inc, 141 pages total.; retrieved from the Internet: <http://www.licor.com/env/PDF/EddyCovariance_readonly.pdf>.

Burba et al., "Combining the Strengths of Open-Path and Closed-Path Designs into a Single CO2/H2O Gas Analyzer," American Geophysical Union Fall Meeting, San Francisco, California, Dec. 14-18, 2009.

Burba et al., "Eddy Covariance Fluxes of Carbon Dioxide and Water Measured With New Compact Gas Analyzer," 2nd Integrated Land Ecosystem-Atmosphere Processes Study Science Conference, Melbourne, Australia, Aug. 24-28, 2009.

Burba et al., "Eddy Covariance Measurements of CO2 and H2O Fluxes With New Compact Gas Analyzer," 10th International Congress of Ecology, Brisbane, Australia, Aug. 16-21, 2009.

Burba et al., "Measurements of CO2 and H2O Fluxes with New Enclosed Design and with Modified Open-path Design of Fast Gas Analyzers," European Geosciences Union General Assembly, Vienna, Austria, May 2-7, 2010.

Burba et al., "Measurements of Evapotranspiration and Carbon Dioxide Exchange Using New Compact Closed-Path Gas Analyzer and Eddy Covariance Technique," The 2009 International Annual Meetings of the ASA, CSSA, and SSSA. Pittsburgh, Pennsylvania, Nov. 1-5, 2009.

Burba et al., "New Compact Gas Analyzer for Eddy Covariance Measurements of Carbon Dioxide and Water Vapor Fluxes," 15th WMO/IAEA Meeting of Experts on Carbon Dioxide, Other Greenhouse Gases, and Related Tracer Measurement Techniques. Max-Planck-Institute for Biogeochemistry, Jena, Germany, Sep. 7-10, 2009.

Burba et al, "New CO2/H2O Gas Analyzer Combines the Advantages of Open-Path and Closed-Path Solutions," AsiaFlux-2009, Integrating Cross-scale Ecosystem Knowledge: Bridges and Barriers. Hokkaido University, Sapporo, Japan, Oct. 27-29, 2009.

Burba et al., Poster presentation "Small Closed-Path CO2-H2O Gas Analyzer for Eddy Covariance Measurements.," The 8th International Carbon Dioxide Conference. Max-Planck-Institute for Biogeochemistry, Jena, Germany, Sep. 13-19, 2009.

Burba et al., "New CO2 and H2O Gas Analyzer Design Combines Open-Path and Closed-Path Advantages," 2009 AmeriFlux Principal Investigator Workshop, DOE, Washington DC, Sep. 21-23, 2009.

Burba et al., "New CO2/H2O Gas Analyzer for Eddy Covariance Flux Measurements," 94th Ecological Society of America Annual Meeting, Albuquerque, New Mexico, Aug. 2-7, 2009.

(56) References Cited

OTHER PUBLICATIONS

Burba et al., Novel Design of an Enclosed CO2/H2O Gas Analyze for Eddy Covariance Flux Measurements, *Tellus*, p. 1-6, Jun. 10, Aug. 1-6, 2010.

Burba et al., "Two New Low-Power and Light-Weight Solutions for Fast Measurements of $CO_2$ and $H_2O$ Ecosystem Exchange," 95th Annual Meeting of Ecological Society of America, Pittsburgh, Pennsylvania, 2010.

Clement, R., et al., "Improved Trace Gas Flux Estimation Through IRGA Sampling Optimization", *Agricultural and Forest Meteorology*, vol. 149, Dec. 6, 2008.

Grelle A., et al., "Fine-Wire Thermometer to Correct CO2 Fluxes by Open-Path Analyzers for Artificial Density Fluctuations", *Agricultural and Forest Meteorology*, vol. 147, Jun. 2007.

Lubken et al., "The Effect of Water Vapour Broadening on Methane Eddy Correlation Flux Measurements," Journal of Atmospheric Chemistry, Jul. 1991; 13(1):91-108.

Neftel, Albrecht et al., "N2O exchange over managed grassland: Application of a quantum cascade laser spectrometer for micrometeorological flux measurements," *Agricultural and Forest Meteorology*, (2010) 150:775-785.

Reba, M., et al., "An Assessment of Corrections for Eddy Covariance Measures Turbulent Fluxes Over Snow in Mountain Environments", *Water Resources Research*, vol. 45, Aug. 18, 2009.

Tuzon, B. et al., "Field intercomparison of two optical analyzers for $CH_4$ eddy covariance flux measurements," *Atmos. Meas. Tech. Discus.*, (2010) 3:2961-2993.

Webb, E., et al., Correction of Flux Measurements for Density Effects Due to Heat and Water Vapour Transfer, *Quart. J. R. Met. Soc.*, vol. 106, p. 85-100, 1980.

McDermitt, D.K. et al. "Effects of Temperature, Pressure and Water Vapor on Gas Phase Infrared Absorption by $CO_2$," Poster presentation, Dec. 1993; LI-COR, Inc. Publication, Lincoln, NE 68504, USA (Dec. 2008) (5 pages).

Prosecution history of U.S. Appl. No. 11/776,063, filed Jul. 11, 2007 (as downloaded on Oct. 28, 2013).

Instruction Manual: LI-7500A Open Path C02/H20 Gas Analyzer (partial), Apr. 30, 2011, pp. i-viii, p. 1-1, pp. 4-47-4-50.

Bamberger et al. "Deposition Fluxes of Terpenes Over Grassland", Journal of Geographical Research, vol. 116, No. D14, Jan. 1, 2011, pp. 1-13.

European Patent Office, European Search Report for Application No. EP14185970, May 6, 2015.

* cited by examiner

SYSTEMS AND METHODS FOR MEASURING GAS FLUX

CROSS-REFERENCES TO RELATED APPLICATIONS

Not applicable.

BACKGROUND

The present disclosure relates generally to gas analysis and, more particularly, to systems and methods for measuring gas flux.

The increasing concentrations of carbon dioxide and other traces gases (e.g., $H_2O$, $CH_4$, $N_2O$, $NH_3$, etc.) in the atmosphere, and the resulting greenhouse effect and climate change, have become important topics for scientific research. In order to understand the global carbon balance, it is necessary to determine the rate at which carbon dioxide and energy exchanges between the atmosphere and terrestrial and oceanic ecosystems. The air within a few hundred meters above the earth's surface is mostly turbulent, so that turbulent structures (e.g., vortices of variable sizes) called "eddies" are responsible for the vertical transport of most of the gases, including carbon dioxide and water vapor, and also heat and momentum between the surface and the atmosphere. The rates of such transport can be calculated from simultaneous, high-frequency measurements of the vertical component of wind speed, the concentrations of carbon dioxide and water vapor, and the air temperature. Similar calculations can be made to measure methane or other gases of interest, for example.

One issue involved in computing turbulent gas flux rates is that multiple measurement devices are used to provide the necessary data, including gas analyzers, temperature sensors, wind speed measuring devices, and/or water vapor analyzers, among others. Each of these measurement devices operates on its own clock. In order to properly compute turbulent gas flux rates, the clocks of the different measurement devices used for accumulating data should be synchronized.

In one conventional approach, analog measurement data is transmitted to a data logger that logs the data and then samples the analog data. However, not all measurement devices provide analog outputs.

Another conventional approach provides for a synchronous bus between the measurement devices that synchronizes the clocks of the multiple measurement devices. The main problem with synchronous buses is that they do not scale well. Also, synchronous buses tend to be proprietary to each manufacturer.

Also, in many conventional approaches, the measurement devices and any other devices at the sampling site do not offer any processing or analysis of the raw data. Data is collected over a period of time, for example over two weeks, and is stored at the sampling site, typically in a storage device coupled to or included in one of the measurement devices. A scientist must then go out to the sampling site to retrieve the data on the storage device for analysis. This conventional approach is very cumbersome since going to the sampling site on a repeated basis is tedious and time consuming, and can be dangerous if the sampling is being performed in remote or difficult-to-access locations.

Accordingly, it is desirable to provide systems and methods that overcome the above and other limitations of conventional approaches to measuring gas flux.

SUMMARY

One embodiment provides a system for measuring gas flux. The system includes a measurement subsystem configured to measure environmental data associated with measuring the gas flux, wherein the measurement subsystem comprises at least two clocks, and a processing unit in signal communication with the measurement subsystem. The processing unit is configured to: transmit a signal over a packet-switched network to the measurement subsystem so as to synchronize the at least two clocks in the measurement subsystem, receive the environmental data from the measurement subsystem, wherein the environmental data is associated with the at least two clocks, and calculate the gas flux based on the environmental data received from the measurement subsystem.

Another embodiment provides a computing device for calculating gas flux. The computing device includes: a first interface configured to receive a master clock signal from a global positioning system (GPS) module; a second interface configured to transmit a clock synchronization signal that is based on the master clock signal to a measurement subsystem configured to measure environmental data, wherein the measurement subsystem comprises at least two clocks; a third interface configured to receive the environmental data from the measurement subsystem, wherein the environmental data is associated with the at least two clocks; and a processing unit configured to calculate gas flux based on the environmental data received from the measurement subsystem.

Yet another embodiment provides a method for calculating gas flux. The method includes: receiving a master clock signal from a global positioning system (GPS) module; transmitting a clock synchronization signal that is based on the master clock signal to a measurement subsystem configured to measure environmental data, wherein the measurement subsystem comprises at least two clocks; receiving the environmental data from the measurement subsystem, wherein the environmental data is associated with the at least two clocks; and calculating gas flux based on the environmental data received from the measurement subsystem.

Reference to the remaining portions of the specification, including the drawings and claims, will realize other features and advantages of the present disclosure. Further features and advantages of the present disclosure, as well as the structure and operation of various embodiments of the present disclosure, are described in detail below with respect to the accompanying drawings. In the drawings, like reference numbers indicate identical or functionally similar elements.

DETAILED DESCRIPTION

Embodiments of the disclosure provide systems and methods for measuring gas flux based on synchronizing hardware clocks included in two or more measurement instruments. Each measurement instrument includes a software clock and a hardware clock. A computing subsystem is communicatively coupled to the measurement instruments and also to a GPS (global positioning system) module. The GPS module is configured to send pulses to the computing subsystem with GPS data that includes time data. A controller included in the computing subsystem is configured to receive the pulses from the GPS module and to set a master clock included in the computing subsystem.

The computing subsystem is configured to synchronize the software clocks of the measurement instruments to the master clock via a packet-switched network. Each measurement instrument further includes a controller that is configured to synchronize the hardware clock included in the measurement instrument to the synchronized software clock included in the measurement instrument. Raw data that is output by the measurement instruments, which is now synchronized in time, is then transmitted to the computing subsystem for computation or further processing. Gas flux measurements are computed based on the raw data. The computed gas flux measurements are then transmitted to one or more of the measurement instruments and/or to a monitoring software device for storage, analysis, and consumption.

Advantageously, embodiments of the disclosure provide for real-time or near real-time gas flux measurements. Also, the disclosed system synchronizes the clocks over an asynchronous network (such as, for example, Ethernet), which provides for ease of installation and maintenance.

Figure 1:
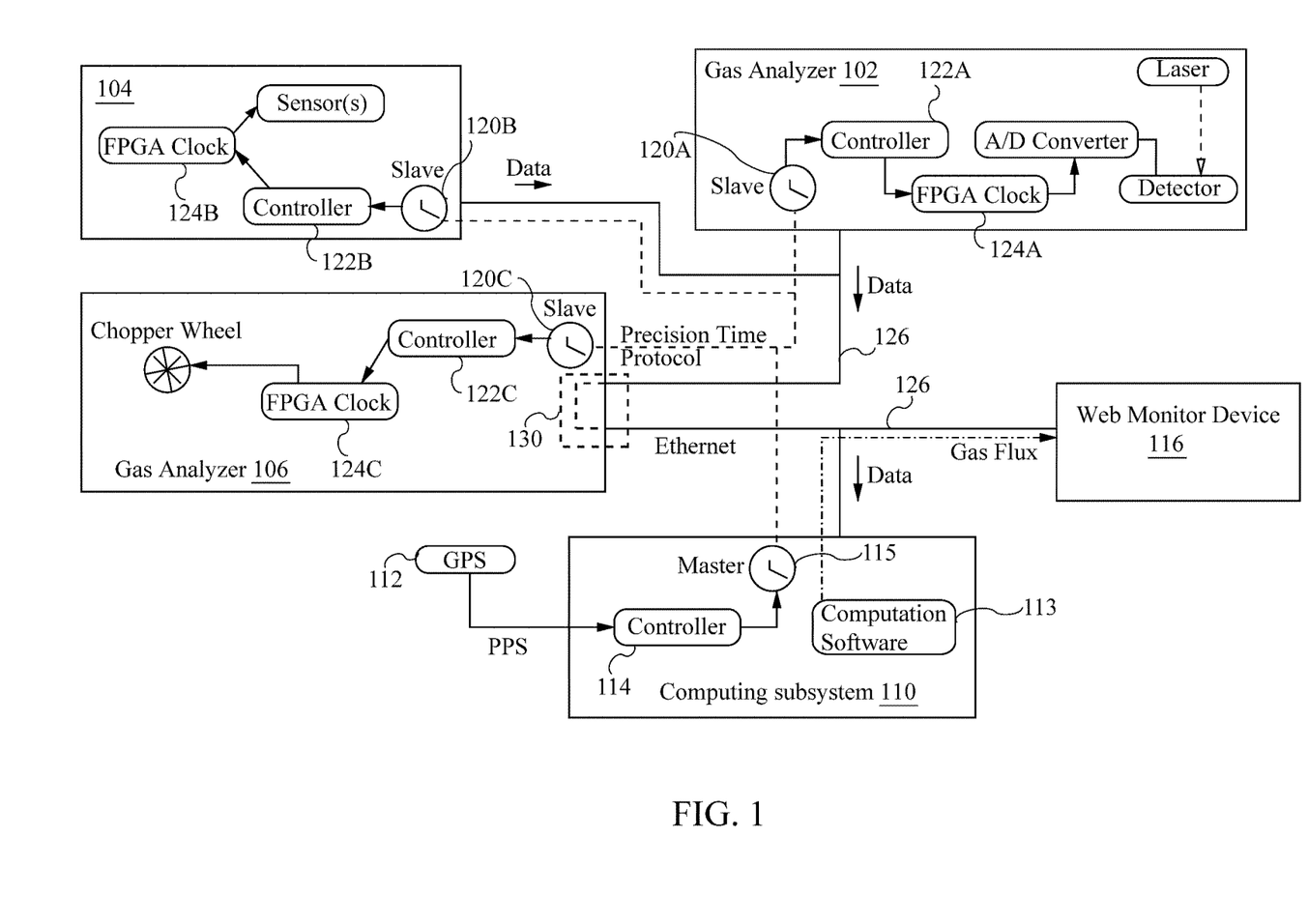
FIG. 1 illustrates a gas flux measurement system, according to one embodiment.

FIG. 1 illustrates a gas flux measurement system, according to one embodiment. As shown, the system includes gas analyzer 102, gas analyzer 106, wind speed measuring device 104, computing subsystem 110, and web monitor device 116, which are interconnected via a data communication path 126. The system also includes a GPS (global positioning system) module 112 communicatively coupled to the computing subsystem 110.

The data communication path 126 can be physical wires/cabling, or a form of wireless communication link (e.g., radio, WiFi, cellular data connection, satellite data connection, etc.), or some combination of both. In one embodiment, the data communication path 126 comprises an Ethernet connection.

The gas analyzer 102 can be any analyzer suitable for measuring the density of a target gas, i.e., the gas of interest that is to be analyzed. For example, methane ($CH_4$) is a commonly measured gas. Methane analyzers for measuring methane density are commercially available, such as the LI-7700 Open Path $CH_4$ Analyzer, which is designed, manufactured, and sold by the assignee of the present application. Generally, absorption-based gas analyzers use absorption of light from either (i) a broadband non-dispersive infrared (NDIR) source equipped with suitable optical filter, or (ii) a narrowband laser source to measure the density of the target gas of interest. The light is selectively absorbed by the gas as it crosses the light path between the light source and a detector in a region called the sampling volume (also variously referred to as "sample volume," "sampling path," and so on). The gas analyzer 102 outputs raw gas density measurement data via the data communication path 126 based on the measured absorption characteristics.

Two categories of gas analyzers are conventionally known and are defined by the nature of the sampling volume. An "open path" type gas analyzer is one in which the sampling volume and the optical path are exposed to the environment containing the gas to be analyzed. A "closed path" gas analyzer is one in which the sampling volume is enclosed in a tube (in which case the sampling volume can be referred to as the sample cell) and the optical path lies within the tube, and the gas to be measured is passed within the tube. In accordance with the present application, the gas analyzer 102 can be either an open path analyzer or a closed path analyzer or a combination of the two.

Gas analyzer 106 can also be any analyzer suitable for measuring the density of a target gas. In one embodiment, gas analyzer 106 is configured to measure carbon dioxide ($CO_2$) gas and water vapor ($H_2O$). One example of such a gas analyzer is the LI-7550 Analyzer, which is designed, manufactured, and sold by the assignee of the present application. For example, the gas analyzer 106 may be a high-speed, high-precision, non-dispersive infrared gas analyzer that accurately measures densities of carbon dioxide and water vapor in situ. For example, a chopper wheel carrying a plurality of spectral filters sequentially passes radiation from a source at discrete wave-lengths through each cell in sequence. The amount of radiation absorbed by the gas is detected to determine the concentrations of certain components in the gas. The gas analyzer 106 outputs raw gas density measurement data via the data communication path 126 based on the measured absorption characteristics.

The wind speed measuring device 104 produces a measure of the speed of the moving air in the vicinity of the gas analyzer 102 and/or gas analyzer 106 and outputs corresponding wind speed measurement data via the data communication path 126. In some embodiments, the wind speed measurement in accordance with the present disclosure may be vertical wind speed. An instrument commonly used to measure wind speed is known as an anemometer. This instrument is commonly used with open path gas analyzers, for example. There are several types of anemometers, ranging in complexity. The most basic models of anemometers measure the wind speed, while the more complex models can measure wind speed, wind direction, and/or atmospheric pressure. One particularly useful type of anemometer is a sonic anemometer that typically provides high-speed (e.g., more than 10 Hz) measurements. It will be appreciated of course that other wind speed measurement devices and techniques can be used.

In the embodiment shown in FIG. 1, the raw data output from the gas analyzer 102 via data communication path 126 is transmitted to the gas analyzer 106. The raw data output from the wind speed measuring device 104 via data communication path 126 is also transmitted to the gas analyzer 106. The raw data output by the gas analyzer 106, as well as the raw data received by the gas analyzer 106 from the gas analyzer 102 and the wind speed measuring device 104, are then transmitted via the data communication path 126 to the computing subsystem 110. In one implementation, when the data communication path 126 is an Ethernet connection, an Ethernet switch 130 included in the gas analyzer 106 is configured to receive the raw data from the gas analyzer 102 and the wind speed measuring device 104 and forward the raw data to the computing subsystem 110. As shown, each of the gas analyzer 102 and the wind speed measuring device 104 is connected in series with the gas analyzer 106, which is configured to receive and forward the raw data from the gas analyzer 102 and the wind speed measuring device 104, respectively.

In some embodiments, a storage device (not shown) may be coupled to the gas analyzer 106. For example, the storage device may comprise a USB (Universal Serial Bus) storage device that includes non-volatile memory. The raw measurement data measured by the gas analyzers 102, 106 and by the wind speed measuring device 104 can be stored in the storage device of the gas analyzer 106.

In another embodiment, each of the gas analyzer 102, the wind speed measuring device 104, and the gas analyzer 106 is directly connected to the computing subsystem 110 via the data communication path 126.

Also, in some embodiments, a single gas analyzer is configured to measure methane, carbon dioxide, and water vapor. Such a gas analyzer could be coupled to the computing subsystem 110 via data communications path 126.

In other embodiments, a water vapor analyzer may be used as a separate gas analyzer from a gas analyzer that measures carbon dioxide gas. Such water vapor gas analyzer might include a hygrometer or other analyzer and could be coupled to the computing subsystem 110 via data communications path 126. In certain environments, the water content can be significant enough to considerably affect the absorption lineshape of the target gas and the resulting density measurement. Dilution by water vapor causes an actual physical change in partial pressure and a change in actual density when compared to dry. In addition, water vapor affects absorption by line broadening, which consequently affects the resulting density measurement. Under such conditions, more accurate results are achieved if the water content is measured and factored into the computations. In some embodiments, atmospheric pressure is also measured and is used to obtain a correct gas concentration measurement. U.S. Pat. No. 8,433,525, which is hereby incorporated by reference in its entirety, provides a more detailed discussion regarding such water vapor effects on measurements. However, if the environment where the target gas is being analyzed is sufficiently dry, the water content may not have any significant affect on density measurements of the target gas. In that case, the cost and complexity of coordinating gas density measurements with water vapor measurements can be dispensed with and the water vapor analyzer would not be required.

In some embodiments, a temperature sensor (not shown) may be used to measure ambient temperature in the proximity of the gas density measurements. Typical devices for the temperature sensor include a fine-wire thermocouple, a sonic anemometer, and in general any device that can provide fast gas temperature measurements. In accordance with the present disclosure, the temperature sensor can be positioned in proximity to the sampling volume of the gas analyzers 102 and/or 106, or alternatively within the sampling volume of the gas analyzers 102 and/or 106. Any other type of measurement device can also be used and is within the scope of embodiments of the disclosure.

As shown in FIG. 1, the gas analyzer 102, the wind speed measuring device 104, and the gas analyzer 106 communicate data to the computing subsystem 110 via the data communication path 126. The computing subsystem 110 includes a suitable data processing component (e.g., one or more processors), data storage devices, and communication interfaces. The computing subsystem 110 may include many more components than those shown in FIG. 1. However, it is not necessary that all of these generally conventional components be shown in order to disclose illustrative embodiments for practicing the present disclosure.

Typical devices that can serve as the data storage device include traditional disk storage devices such as hard disk drives, floppy disk drives, writable CD-ROMs, other removable storage formats, and the like. Data storage can also include flash memory devices such as flash drives, or other similar static storage devices. Data storage is typically a high capacity storage device for storing the large amounts of measurement data that can be received by the computing subsystem 110 during a data collection session. The data storage may be called upon to store data from several data collection sessions.

The computing subsystem 110 can be configured to any level of sophistication as needed for a particular implementation of the measurement devices shown in the system of FIG. 1, and can be built to survive rugged field deployments for months or even years on end.

In accordance with some embodiments, the computing subsystem 110 can be a full-featured and sophisticated data logging component that is not only able to communicate with the measurement devices via the data communication path 126 and receive measurement data from the measurement devices to be stored in the data storage, but also includes computer program code, such as computation software 113, to calculate gas flux values of the target gas of interest. The target gas of interest can be carbon dioxide, water vapor, methane, or any other gas. In one embodiment, the computing subsystem 110 is located at the same measurement site as the measurement devices (i.e., the same measurement site as the gas analyzers 102 and/or 106, and the wind speed measuring device 104).

According to various embodiments, the Eddy Covariance (EC) method is the most direct and reliable method for gas flux measurement calculations available to date. EC is a dominating method used in most turbulent flux measurements. EC is used as a standard for other turbulent flux measurement methods, and for any atmospheric flux measurement methods. However, EC requires high-speed gas concentration measurements (e.g., 5-10 Hz (Hertz) or more) in addition to the high-speed vertical wind speed measurements (e.g., 5-10 Hz or more). The computation software 113 is configured to receive the gas concentration measurements and the vertical wind speed measurements and calculate the gas flux values therefrom. The calculated gas flux values may be computed as a gas flux based on measurement taken over a certain time period, for example, 30 minutes. The calculated gas flux values can then be transmitted via the data communication path 126 to the gas analyzer 106 for storage in a storage device and/or may be transmitted via the data communication path 126, or another data communication path (not shown) to the web monitor device 116. In some embodiments, the web monitor device 116 is located at a remote location from the measurement site. Because the calculated gas flux values are relatively small in data size compared to the high-speed gas concentration measurements and vertical wind speed measurements, the data connection by which the calculated gas flux values are transmitted to one or more measurement devices and/or a remote computing device can be a small-bandwidth connection. Examples of data connections that could be used include Ethernet, cellular network, or satellite network, among others.

In some embodiments, the data communication path between the computing subsystem 110 and the measurement devices (i.e., the gas analyzers 102 and/or 106 and the wind speed measuring device 104) is different from the data communication path between the computing subsystem 110 and the web monitor device 116. In some embodiments, the data communication paths are the same.

As also shown in FIG. 1, computing subsystem 110 includes a master clock 115 and controller 114. The controller 114, which may be implemented as a proportional-integral (PI) control system, is configured to receive data pulses from the GPS module 112. The pulses may be PPS (pulse-per-second) pulses. The controller 114 is configured to set the master clock 115 included in the computing subsystem 110 according to the data pulses from the GPS module 112. The master clock 115 can be a software clock or a hardware clock.

As also shown, gas analyzer 102, wind speed measuring device 104, and gas analyzer 106 include slave clocks 120A, 102B, and 120C, respectively. In some embodiments, the slave clocks 120A-120C comprise software clocks.

Gas analyzer 102, wind speed measuring device 104, and gas analyzer 106 further include controllers 122A, 122B, and 122C, respectively. In some embodiments, controllers 122A-122C may be similar to the controller 114 included in the computing subsystem 110.

Gas analyzer 102, wind speed measuring device 104, and gas analyzer 106 further include hardware clocks 124A, 124B, and 124C, respectively. In one embodiment, the hardware clocks 124A-124C are implemented as FPGAs (field-programmable gate arrays).

In order for the computing subsystem 110 to accurately compute gas flux values, the measurement data measured by the various measurement devices should be synchronized in time. As such, the hardware clocks 124A-124C should be synchronized.

The IEEE 1588 protocol, "Standard for a Precision Clock Synchronization Protocol for Networked Measurement and Control Systems" (also referred to as, "Precision Time Protocol") was developed to enable synchronizing clocks between devices connected by a network. Using the IEEE 1588 protocol, to achieve the highest precision, for example in the nanosecond range, dedicated hardware is used that detects synchronization packets on the network and adjusts a clock accordingly. In conventional approaches to clock synchronization, a software-only implementation of IEEE 1588 is available in an open source application called "PTPd" (Preciscion Time Protocol daemon). PTPd is able to synchronize the software system clocks on multiple systems with microsecond precision. PTPd does not control a hardware clock, but adjusts the time-of-day value in the operating system. As such, the IEEE 1588 protocol and the PTPd technique can be used to synchronize the software clocks 120A-120C included in the measurement devices to the master clock 115 via a packet-switched network, such as Ethernet.

Embodiments of the disclosure build on top of such a software-only implementation of IEEE 1588 (such as PTPd). First, the master clock 115 is synchronized to the PPS pulse from the GPS module 112 by the controller 114. Then, the software clocks 120A-120C included in the measurement devices are synchronized to the master clock 115 using a software-only implementation of IEEE 1588 (such as PTPd). Once the software clocks 120A-120C included in the measurement devices are synchronized to one another, the corresponding controllers 122A-122C, respectively, are configured to synchronize the hardware clocks 124A-124C to the corresponding software clocks 120A-120C, respectively. As such, the hardware clocks 124A-124C become synchronized to one another. The measurement data collected by the measurement devices is now synchronized in time.

The measurement data can be transmitted to the computing subsystem 110 for computation of gas flux values, as described above. The results can be transmitted back to the measurement devices for storage or to the web monitor device 116, as also described above, where the results may be displayed.

As such, embodiments of the disclosure provide systems and methods for computing gas flux values in real-time or near-real-time using instruments connected over Ethernet. In further embodiments, the clock synchronization method disclosed herein could also be used in any device generating a data stream to allow that data to be merged with data from another device.

Figure 2:
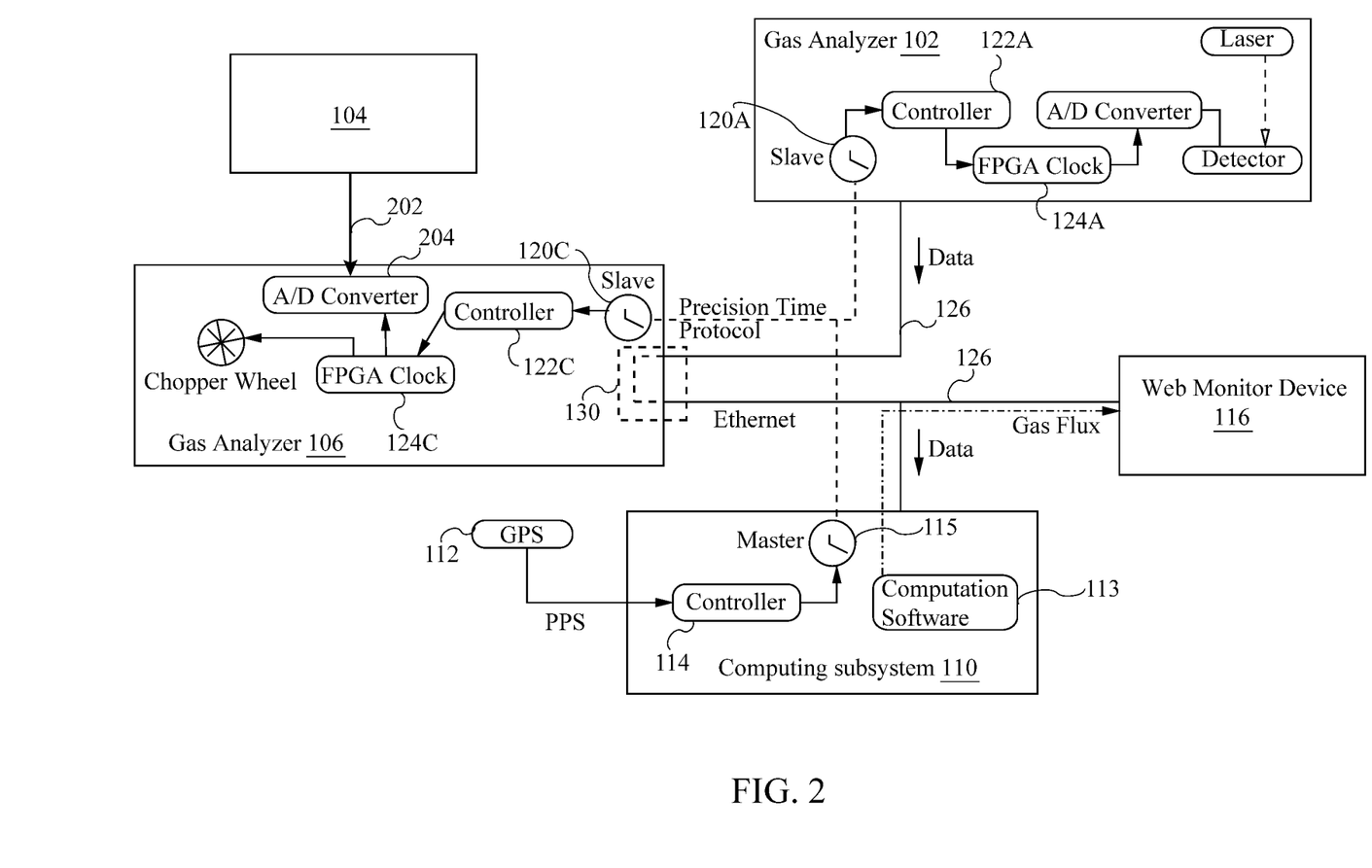
FIG. 2 illustrates a process of measuring gas flux, according to one embodiment.

FIG. 2 illustrates a gas flux measurement system, according to one embodiment. Many of the components shown in FIG. 2 are described in FIG. 1 and are not repeated for clarity. One difference between FIG. 1 and FIG. 2 is that in FIG. 2, the wind speed measuring device 104 is not connected to the gas analyzer 106 via the data communication path 126 (nor is the wind speed measuring device 104 connected directly to the computing subsystem 110 via the data communication path 126). Rather, the wind speed measuring device 104 is connected to the gas analyzer 106 via an analog connection 202. As such, an analog-to-digital (A/D) converter 204 included in the gas analyzer 106 is configured to sample the raw analog wind data received from the wind speed measuring device 104. The raw data can be sampled based on the hardware clock 124C included in the gas analyzer 106. As described above, the hardware clock 124C is synchronized to the other hardware clocks 124A-124B included in the system by way of the corresponding software clocks, and ultimately by way of the master clock 115 and pulses from the GPS module 112.

Figure 3:
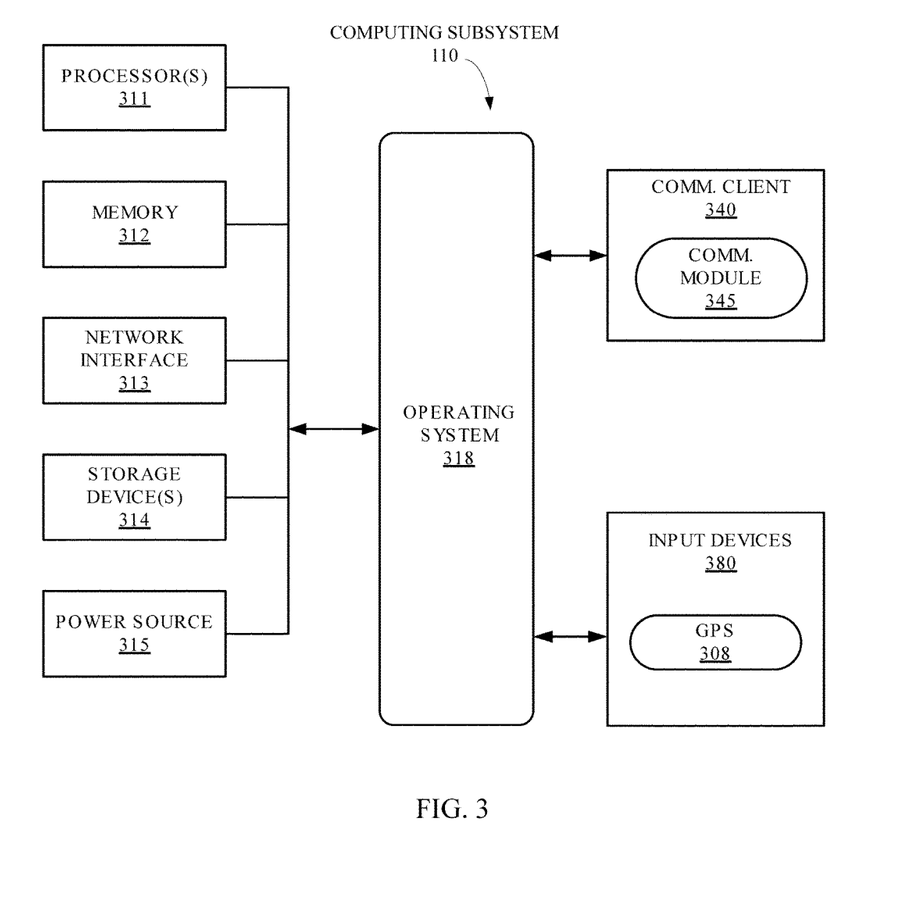
FIG. 3 is a block diagram of example functional components for a computing subsystem, according to one embodiment.

FIG. 3 is a block diagram of example functional components for a computing subsystem 110, according to one embodiment. One particular example of computing subsystem 110 is illustrated. Many other embodiments of the computing subsystem 110 may be used. In the illustrated embodiment of FIG. 3, the computing subsystem 110 includes one or more processor(s) 311, memory 312, a network interface 313, one or more storage devices 314, a power source 315, and input device(s) 380. The computing subsystem 110 also includes an operating system 318 and a communications client 340 that are executable by the client. Each of components 311, 312, 313, 314, 315, 360, 380, 318, and 340 is interconnected physically, communicatively, and/or operatively for inter-component communications in any operative manner.

As illustrated, processor(s) 311 are configured to implement functionality and/or process instructions for execution within computing subsystem 110. For example, processor(s) 311 execute instructions stored in memory 312 or instructions stored on storage devices 314. Memory 312, which may be a non-transient, computer-readable storage medium, is configured to store information within computing subsystem 110 during operation. In some embodiments, memory 312 includes a temporary memory, area for information not to be maintained when the computing subsystem 110 is turned OFF. Examples of such temporary memory include volatile memories such as random access memories (RAM), dynamic random access memories (DRAM), and static random access memories (SRAM). Memory 312 maintains program instructions for execution by the processor(s) 311, such as the computation software 113 shown in FIGS. 1-2 for computing gas flux from measurement data.

Storage devices 314 also include one or more non-transient computer-readable storage media. Storage devices 314 are generally configured to store larger amounts of information than memory 312. Storage devices 314 may further be configured for long-term storage of information. In some examples, storage devices 314 include non-volatile storage elements. Non-limiting examples of non-volatile storage elements include magnetic hard disks, optical discs, floppy discs, flash memories, or forms of electrically programmable memories (EPROM) or electrically erasable and programmable (EEPROM) memories.

The computing subsystem 110 uses network interface 313 to communicate with external devices via one or more networks, such as the gas analyzers 102, 106 and wind speed measuring device 104 shown in FIGS. 1-2. Network interface 313 may be a network interface card, such as an Ethernet card, an optical transceiver, a radio frequency transceiver, or any other type of device that can send and receive information. Other non-limiting examples of network interfaces include wireless network interface, Bluetooth®, 3G and WiFi® radios in mobile computing devices, and USB (Universal Serial Bus). In some embodiments, the computing subsystem 110 uses network interface 313 to wirelessly communicate with an external device, a mobile phone of another, or other networked computing device, such as web monitor device 116.

The computing subsystem 110 includes one or more input devices 380. Input devices 380 are configured to receive input from one or more sources. Non-limiting examples of input devices 380 include a GPS module 308, or any other type of device for detecting a command or sensing the environment.

The computing subsystem 110 includes one or more power sources 315 to provide power to the computing subsystem 110. Non-limiting examples of power source 315 include single-use power sources, rechargeable power sources, and/or power sources developed from nickel-cadmium, lithium-ion, or other suitable material. In some embodiments, the power source 315 is a solar power source. Also, in some embodiments, the power source 315 can be internal to or external to the computing subsystem 110. Also, in some embodiments, power source 315 provides power to the computing subsystem 110 as well as to the measurement devices (e.g., devices 102, 104, 106).

The computing subsystem 110 may include an operating system 318. The operating system 318 controls operations of the components of the computing subsystem 110. For example, the operating system 318 facilitates the interaction of communications client 340 with processors 311, memory 312, network interface 313, storage device(s) 314, input device 180, output device 160, and power source 315. For example, the operating system 318 may control the master clock 115 of the computing subsystem 110.

As also illustrated in FIG. 3, the computing subsystem 110 includes communications client 340. Communications client 340 includes communications module 345. Each of communications client 340 and communications module 345 includes program instructions and/or data that are executable by the computing subsystem 110. For example, in one embodiment, communications module 345 includes instructions causing the communications client 340 executing on the computing subsystem 110 to perform one or more of the operations and actions described in the present disclosure. In some embodiments, communications client 340 and/or communications module 345 form a part of operating system 318 executing on the computing subsystem 110.

Figure 4:
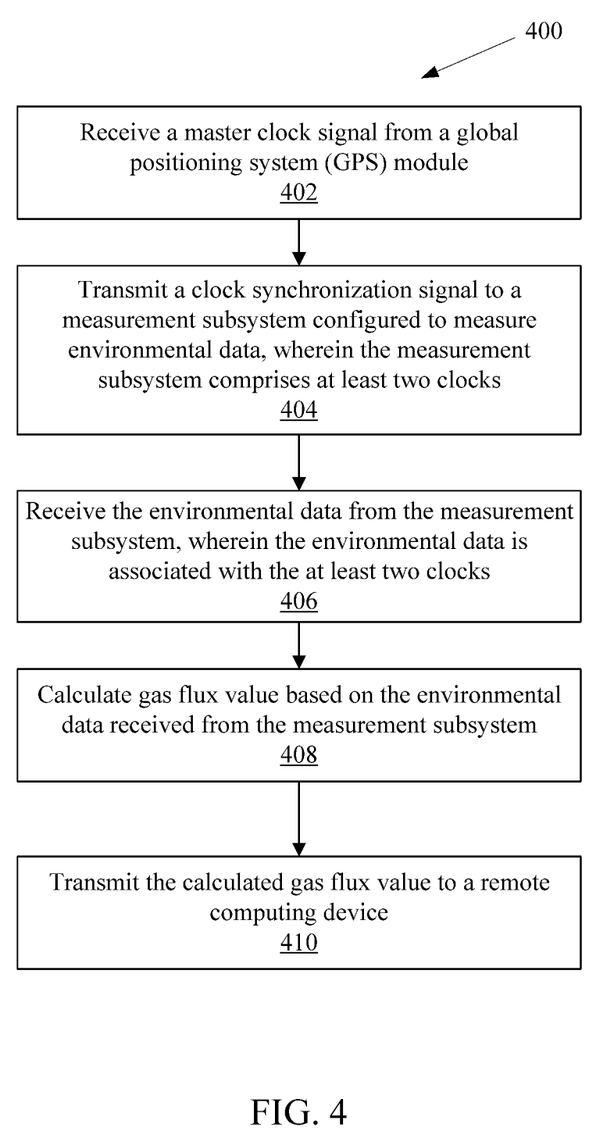
FIG. 4 is a flow diagram of method steps for measuring gas flux, according to one embodiment.

FIG. 4 is a flow diagram of method steps for measuring gas flux, according to one embodiment. As shown, the method 400 begins at step 402, where a computing device, such as computing subsystem 110, receives a master clock signal from a global positioning system (GPS) module. The master clock signal may be a PPS pulse. The computing device uses the master clock signal to set a master clock included in the computing device.

At step 404, the computing device transmits a clock synchronization signal to a measurement subsystem configured to measure environmental data, where the measurement subsystem comprises at least two clocks. In one embodiment, the clock synchronization signal is transmitted over a packet-switched network, such as Ethernet. For example, the measurement subsystem may comprise two or more measurement devices, such as gas analyzers, wind analyzers, temperature analyzers, etc., configured to measure the environment. Each measurement device may include its own hardware clock.

As described herein, in some embodiments, each measurement device is configured to receive the clock synchronization signal from the computing device and synchronize its own software clock to the master clock. Then, by way of a controller included in the measurement device, each measurement device is configured to synchronize a hardware clock included in the measurement device to the corresponding software clock. The environment is sensed based on the timing information from the hardware clocks.

At step 406, the computing device receives the environmental data from the measurement subsystem, where the environmental data is associated with the at least two clocks. At step 408, the computing device calculates one or more gas flux values based on the environmental data received from the measurement subsystem. At step 410, the computing device transmits the calculated gas flux values to a remote computing device, via a data connection, where the gas flux value(s) may be displayed or further processed. Alternatively, the measured (and synchronized) environmental data may be transmitted to a remote computer system for further processing and calculation/computation.

Figure 5:
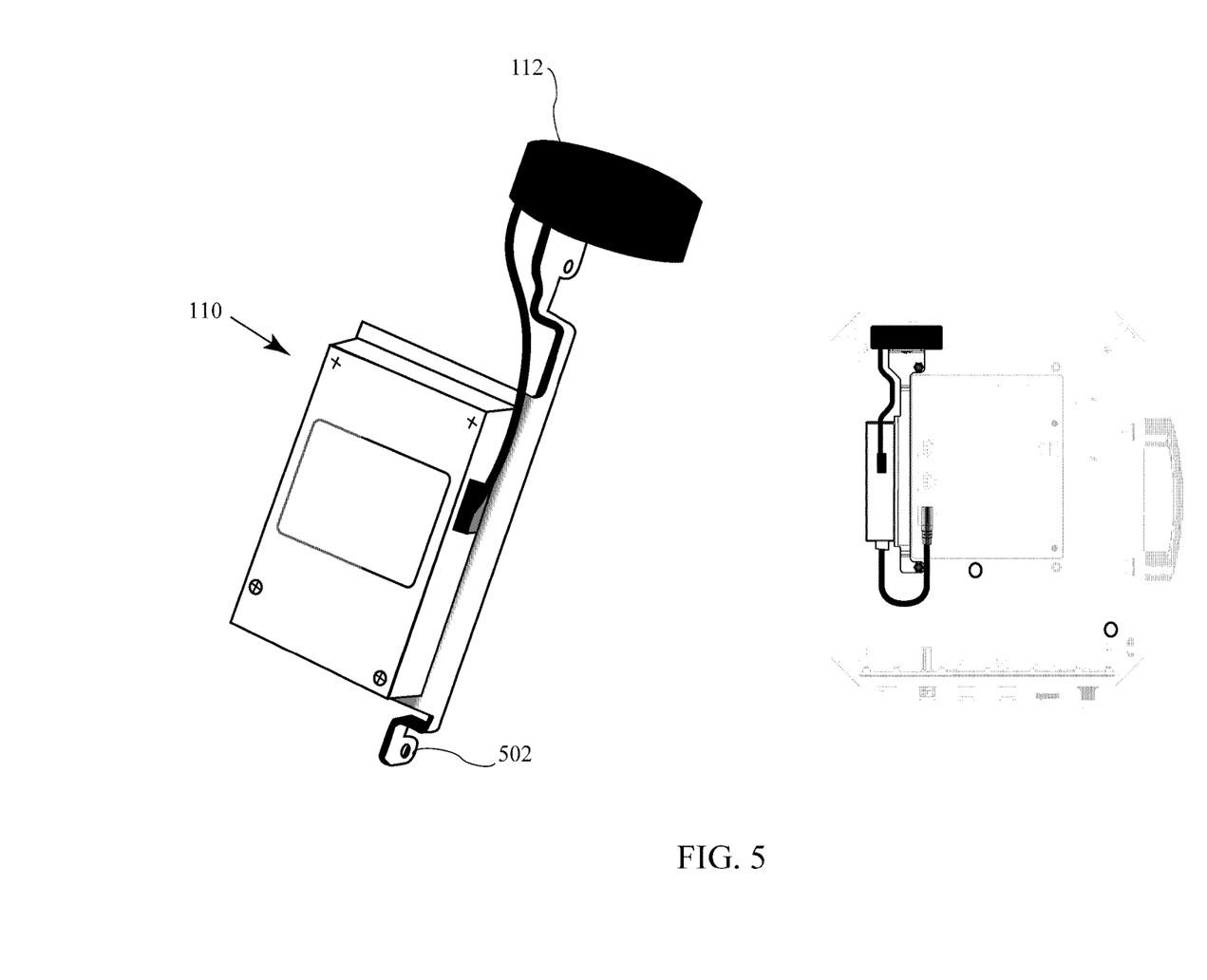
FIG. 5 is a conceptual diagram of a computing subsystem, according to one embodiment.

FIG. 5 is a conceptual diagram of a computing subsystem 110, according to one embodiment. As shown, the computing subsystem 110 is coupled to a GPS receiver 112. The computing subsystem 110 may have a small volumetric footprint, so as to be easily mounted to a gas analyzer via a mounting bracket 502, as also shown in FIG. 5. The example shown in FIG. 5 is merely an example of a computing subsystem 110 and does not limit the scope of embodiments of the disclosure.

In sum, embodiments of the disclosure provide systems and methods for synchronization, management, and real-time or near-real-time calculation of gas flux. The systems and methods can be fully integrated with commercially available analyzers and analyzer interface units. The systems and methods provide fully corrected, real-time flux computations, remote access via a data connection (e.g., cellular or satellite modem, for example), built-in GPS for synchronizing data, precision clock control, coordinate information, inter-site data comparison, a low power draw, rugged construction, and rapid communication via Ethernet. According to various embodiments, integrated data transfer and file viewing software within the computing subsystem 110 and/or web monitor device 116 allows for automated data transfer at user-specified intervals, site monitoring, diagnostics, and charting. Conventional systems that only "estimate" flux rates can introduce large errors when compared to the disclosed systems and methods, which use final, fully corrected flux rates processed by computation software.

Advantageously, the disclosed system synchronizes the clocks of various measurement devices over an asynchronous, packet-switched network (such as Ethernet), which provides for ease of installation and maintenance when providing a gas flux measurement system and method. For example, one advantage to using Ethernet is that a system implementing embodiments of the disclosure can connect many Ethernet devices together from different manufactures and scale up the system easily.

While the present disclosure has been described by way of example and in terms of the specific embodiments, it is to be understood that the present disclosure is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

All references, including publications, patent applications and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

One embodiment of the disclosure may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

We claim:

1. A system for measuring gas flux, the system comprising:
   a measurement subsystem configured to measure environmental data associated with measuring the gas flux, wherein the environmental data comprises at least vertical wind speed data and gas concentration data, wherein the measurement subsystem comprises at least two measurement devices, and wherein the measurement subsystem comprises at least two software clocks and at least two hardware clocks;
   a processing unit in signal communication with the measurement subsystem; and
   wherein the processing unit is configured to:
   transmit a clock synchronization signal over a packet-switched network to each of the at least two measurement devices included in the measurement subsystem so as to synchronize the at least two hardware clocks in the measurement subsystem, wherein the clock synchronization signal is based on the master clock signal, wherein the at least two software clocks are synchronized based on the clock synchronization signal, and wherein each of the at least two hardware clocks is synchronized by a corresponding one of the at least two software clocks,
   receive the environmental data from the measurement subsystem, wherein the environmental data is associated with the at least two hardware clocks, and
   calculate the gas flux based on the synchronized environmental data received from the measurement subsystem.

2. The system of claim 1, wherein the system is installed above a terrestrial surface or a water surface.

3. The system of claim 1, wherein the environmental data comprises gas data and wind data.

4. The system of claim 1, wherein the measurement subsystem comprises a gas analyzer configured to analyze carbon dioxide and water vapor.

5. The system of claim 4, wherein the measurement subsystem further comprises an anemometer.

6. The system of claim 1 wherein the measurement subsystem comprises a first gas analyzer, a second gas analyzer, and an anemometer, wherein the first gas analyzer is configured to analyze methane and the second gas analyzer is configured to measure carbon dioxide and water vapor.

7. The system of claim 1, further comprising:
   a global positioning system (GPS) module communicatively coupled to the processing unit, wherein the GPS module is configured to transmit a signal to the processing unit that corresponds to a master clock signal.

8. The system of claim 7, wherein the signal comprises a PPS (pulse-per-second) signal.

9. The system of claim 1, further comprising a global positioning system (GPS) module communicatively coupled to the processing unit wherein the processing unit is configured to:
   receive a master clock signal from the GPS module, wherein the clock synchronization signal is based on the master clock signal.

10. The system of claim 1, wherein the packet-switched network comprises an Ethernet network.

11. The system of claim 1, wherein the processing unit is further configured to:

transmit the calculated gas flux to a computing device communicatively coupled to the processor over a data network.

12. The system of claim 11, wherein the data network is a wireless network or a wired network.

13. The system of claim 11, wherein the packet-switched network is the same as the data network, or wherein the packet-switched network is different than the data network.

14. The system of claim 1, wherein the measurement subsystem comprises a first device and a second device;
  wherein environmental data measured by a first device is transmitted to the second device; and
  wherein the second device transmits the environmental data measured by the first device to the processing unit.

15. The system of claim 1, wherein each of the at least two hardware clocks includes a field-programmable gate array (FPGA) clock.

16. A computing device for calculating gas flux, the computing device comprising:
  a first interface configured to receive a master clock signal from a global positioning system (GPS) module;
  a second interface configured to transmit a clock synchronization signal that is based on the master clock signal to a measurement subsystem configured to measure environmental data, wherein the environmental data comprises at least vertical wind speed data and gas concentration data, wherein the measurement subsystem comprises at least two software clocks and at least two hardware clocks, wherein the at least two software clocks are synchronized based on the received clock synchronization signal, and wherein each of the at least two software clocks sends a hardware clock synchronization signal to a corresponding one of the at least two hardware clocks, wherein each hardware clock is synchronized based on the received hardware clock synchronization signal;
  a third interface configured to receive the environmental data from the measurement subsystem, wherein the environmental data is associated with the at least two hardware clocks; and
  a processing unit configured to calculate gas flux based on the synchronized environmental data received from the measurement subsystem.

17. The computing device of claim 16, wherein the measurement subsystem comprises a gas analyzer and an anemometer, wherein the gas analyzer is configured to analyze carbon dioxide and water vapor.

18. The method of claim 16, wherein each of the at least two hardware clocks includes a field-programmable gate array (FPGA) clock.

19. A method for calculating gas flux, comprising:
  receiving a master clock signal from a global positioning system (GPS) module;
  transmitting a clock synchronization signal that is based on the master clock signal to a measurement subsystem configured to measure environmental data, wherein the environmental data comprises at least vertical wind speed data and gas concentration data, wherein the measurement subsystem comprises at least two software clocks and at least two hardware clocks, wherein the at least two software clocks are synchronized based on the received clock synchronization signal, and wherein each of the at least two software clocks sends a hardware clock synchronization signal to a corresponding one of the at least two hardware clocks, wherein each hardware clock is synchronized based on the received hardware clock synchronization signal;
  receiving the environmental data from the measurement subsystem, wherein the environmental data is associated with the at least two hardware clocks; and
  calculating gas flux based on the synchronized environmental data received from the measurement subsystem.

20. The method of claim 19, further comprising transmitting the calculated gas flux to a computing device over a data network.

21. The method of claim 19, wherein the measurement subsystem comprises a gas analyzer and an anemometer, wherein the gas analyzer is configured to analyze carbon dioxide and water vapor.

22. The method of claim 19, wherein each of the at least two hardware clocks includes a field-programmable gate array (FPGA) clock.

* * * * *